United States Patent [19]

Pitner et al.

[11] Patent Number: 5,367,058

[45] Date of Patent: Nov. 22, 1994

[54] MODIFIED ANTIBODIES WITH INCREASED AFFINITY

[75] Inventors: J. Bruce Pitner; Linn, Jr. C. Preston; Patrick D. Mize, all of Durham, N.C.

[73] Assignee: Becton Dickinson and Company, Franklin Lakes, N.J.

[21] Appl. No.: 111,699

[22] Filed: Aug. 25, 1993

[51] Int. Cl.$^5$ .............................................. C07K 15/28
[52] U.S. Cl. ........................... 530/391.9; 530/391.7; 530/387.1; 530/388.4
[58] Field of Search ............... 530/391.9, 391.7, 387.1, 530/388.4

[56] References Cited

U.S. PATENT DOCUMENTS 5,215,889  6/1993  Schultz .................. 435/41

FOREIGN PATENT DOCUMENTS

WO90/05749  5/1990  WIPO .

OTHER PUBLICATIONS

Pollack, S. J. et al. *Science* 242, 1038–1040 (1988).

Primary Examiner—David L. Lacey
Assistant Examiner—Susan A. Loring
Attorney, Agent, or Firm—David W. Highet

[57] ABSTRACT

The present invention relates to modified antibodies and fragments which display an increased affinity for antigen as compared to the affinity of unmodified antibody for antigen. The most preferred modification is the addition of a thiol group on the surface of the antibody such that a covalent bond forms between the antibody and antigen when they bind to one another.

6 Claims, 12 Drawing Sheets

MODIFICATION OF ANTIBODIES USING AFFINITY LABELLING REAGENTS

FIG-1 MODIFICATION OF ANTIBODIES USING AFFINITY LABELLING REAGENTS

FIG-2 SYNTHESIS OF AFFINITY LABELLING REAGENTS

FIG-3 MALEIMIDE REACTIVE HAPTENS

FIG-7 COMPETITION OF SH MODIFIED McPC-603 WITH PC-MAL AND IMMOBILIZED BSA-PC

MODIFIED ANTIBODIES WITH INCREASED AFFINITY

BACKGROUND OF THE INVENTION

Antibodies are a class of globular proteins which are produced by the immune system as a defense against foreign agents in mammalian systems. These proteins bind their respective antigen or hapten through a collection of non-covalent interactions (hydrophobic, electrostatic and/or hydrogen bonding interactions). The strength of binding between the antigen and the antibody can vary due to the natural elimination or addition of some of these interactions and the resulting affinity constant (Ka) generally varies between about $10^3$ and about $10^{10}$.

Monoclonal antibodies are a subset of antibodies, and are proteins with a single defined structure and defined amino acid sequence. Monoclonal antibodies are known and desired primarily for their specificity of binding; that is their ability to bind only one compound (antigen or hapten) out of many with very similar structures. However, a recurring problem is the identification and isolation of monoclonal antibodies which have not only great specificity, but also high affinity, i.e. tight binding to its antigen or hapten. Monoclonal antibodies with both high specificity and high affinity are generally identified and isolated only by very laborious screening of many hybridoma cell cultures. Alternatively, genetic techniques may be used to alter specific amino acids in the antibody sequence by site-directed mutagenesis or to generate large numbers of mutations for screening purposes by producing libraries of mutations. However, these techniques are also very labor intensive.

Chemical modification of antibodies with antigen-based reagents has been utilized to produce catalytic antibodies as taught in PCT Application WO 90/05749 published May 31, 1990 and U.S. Pat. No. 5,215,889. However, the chemical modifications used to produce catalytic antibodies are specifically defined as functionalities which do not substantially affect binding affinity between the antibody and its antigen.

SUMMARY OF THE INVENTION

The present invention provides a solution to the conventional labor intensive methods for isolating monoclonal antibodies with high affinity as it relates to a chemically modified monoclonal antibody or antibody fragment with an increased affinity for its antigen or hapten. The modification to the antibody is a chemical moiety which is capable of covalently bonding to a functional group of the antigen or a chemical functionality which modifies the antigen upon binding of the antigen and antibody. The affinity of the modified monoclonal antibody is at least 10-fold greater than the affinity of a corresponding unmodified antibody for the same antigen or modified antigen.

BRIEF DESCRIPTION OF THE FIGURES

The various objects, advantages and novel features of the invention will be more readily appreciated from the following detailed description when read in conjunction with the appended figures, in which.

DETAILED DESCRIPTION OF THE INVENTION

The present invention relates to chemically modified antibodies and fragments which exhibit greater affinity for their antigens than the corresponding unmodified antibodies. In order to increase the affinity of the antibody, the modification must be sufficiently proximate to the antigen binding site such that a covalent bond may be formed between the modifying group or moiety and the antigen when it binds to the antibody.

The modified antibodies and fragments are particularly useful for clinical diagnosis of disease, therapeutic applications, and as scavengers for specific antigens such as alkylating agents due to their increased affinity for antigen. Antibody fragments which are useful are those which contain the binding site for the antigen.

The chemical modification of the antibody can be accomplished in a variety of methods which are well-known to those skilled in the art and taught by M. Brinkley, *Bioconjugate Chemistry*, vol. 3, pp. 2-13 (1992), incorporated herein by reference and G. E. Means and R. E. Feaney, *Bioconjugate Chemistry*, vol. 1, pp. 2-12 (1990), also incorporated herein by reference. However, a preferred method for modifying the antibody is to link, with a cleavable tether, the modifying group to the antigen, allow the antigen to bind with the antibody, and then cleave the modifying group from the antigen after it has reacted with the antibody. This method assures that the modifying group will be in sufficient proximity to the antigen binding site such that a covalent bond between the antigen and the modifying group will occur upon reaction of the antigen and the antibody.

Figure 1:
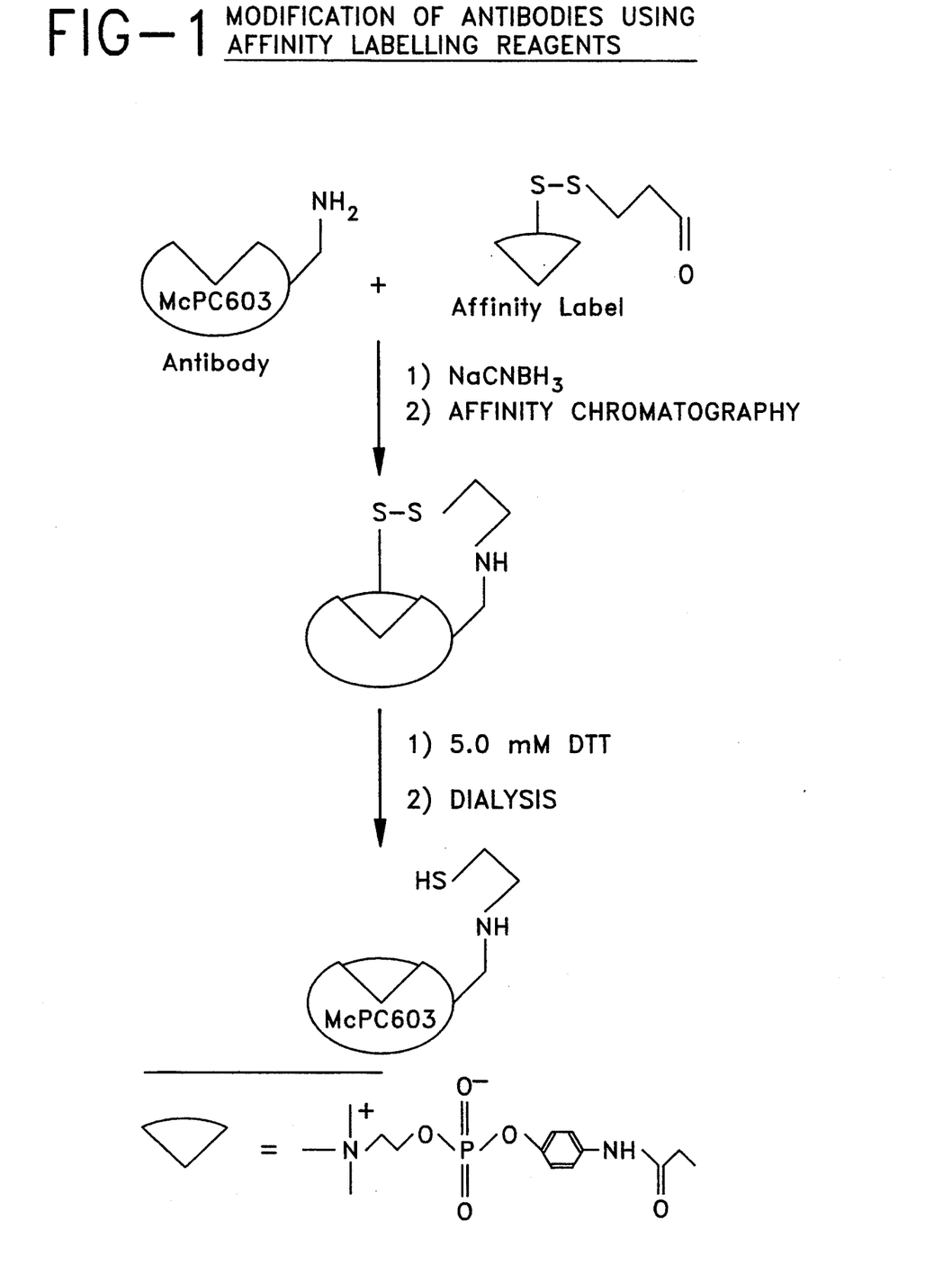
FIG. 1 shows a schematic representation of a process for making a modified phosphorylcholine binding antibody in accordance with one embodiment of the invention.
Figure 2:
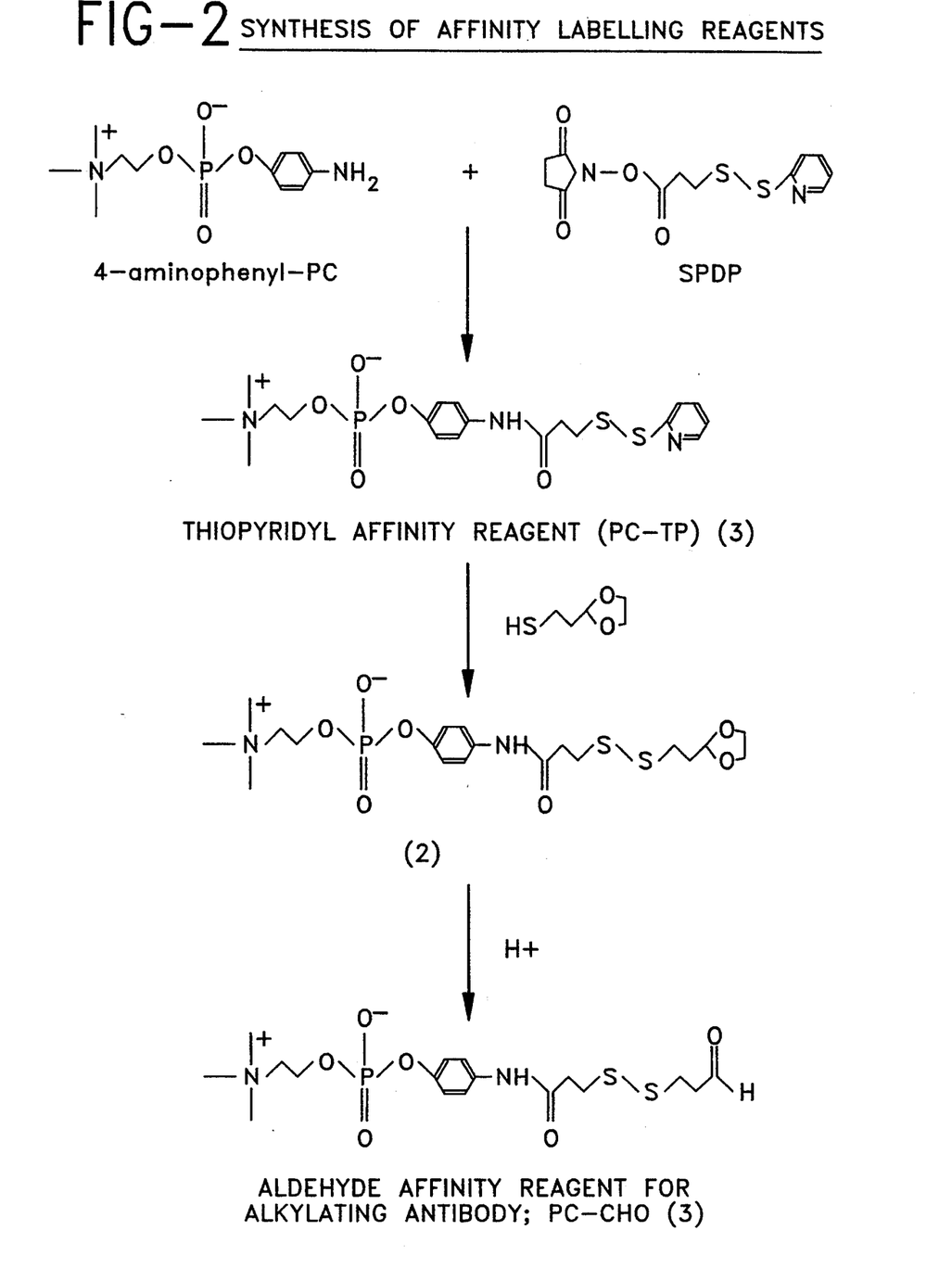
FIG. 2 shows chemical reactions involved in the preparation of a thiopyridyl modified phosphorylcholine antigen (PC-TP), and the subsequent preparation of an aldehyde modified phosphorylcholine antigen (PC-CHO)

The procedure for first modifying the antigen with a cleavable linking group that contains the modifying group for the antibody will vary in accordance with the particular antigen and antibody to be modified. However, the general procedure which is explained in specific detail in the example is illustrated in FIG. 1 in which a cleavable linking group is chemically attached to the antigen in such a manner that the principal binding interactions between the antibody and antigen are left intact to the extent possible. This cleavable linking group may be linked with the antibody modifying group either before this step or afterwards. The modifying group may be masked during these steps, as in the example where an aldehyde is protected as the corresponding dioxolane as shown in FIG. 2.

The principal binding interactions of the antigen and antibody to be left intact or unaltered by the process are determined by x-ray crystallography. For example, for the McPC603 antibody and its antigen, phosphorylcholine (PC), x-ray crystallography (see(a) Y. Satow, et al., *J. Mol. Biol.*, vol. 190, 593–604, (1986) and (2) D. M. Segal, et al, *Proc. Nat. Acad. Sci., USA*, vol., 71, pp. 4298–4302 (1974)) revealed that the positively charged trimethylammonium function of PC is bound in a pocket with negatively charged amino acids, Asp97L and Glu3 SHY, providing an electrostatic attractive force at the pocket's bottom. Similarly, the negatively charged phosphate group of PC is bound primarily by Arg52H. Other nearby amino acids provide more modest contributions to binding and help define the shape of the binding pocket. Thus, the cleavable linking group which is attached to PC must not interfere with PC interaction with Asp97L, Glu35HY, Arg52H and other nearby amino acids of McPC603. Generally, the chemical modifying group (or cleavable linking group which is subsequently convened to the modifying group) interacts with certain functional groups on the antibody surface such as the amino acids lysine and arginine. It has been found that such functional groups on the antibody surface should be within about twenty (20) angstroms and preferably within about 5 to 20 angstroms of the antigen/antibody binding site.

The modifying groups that are effective for increasing the affinity of antibodies for their antigens include thiol-containing groups, activated carboxylic-acid containing groups, amine-containing groups, aldehyde-containing groups, ketone-containing groups, diazo-containing groups, nitrene-containing groups, and carbene-containing groups. The preferred modifying group is the thiol-containing group, and the most preferred modifying group is a thiol group. Other useful modifying groups include boronic acids and diols.

The cleavable linking group which is utilized in the antibody modification process may be any group capable of binding the desired modifying group. However, the cleavable linking group, when bound to the modifying group must be of such a length or in such a configuration that when the antigen is bound at the antibody binding site, the modifying group is in appropriate position to react with an amino acid of the antibody sufficiently close to the antibody binding site such that the modifying group will covalently bind the antigen upon antigen/antibody interaction. The length or configuration of the cleavable linking group can be estimated by constructing computer models of the appropriate structures of the antibody and antigen during interaction. Useful programs for such computer modeling include Sybyl (Tripos, Inc., St. Louis, Mo.) and Quanta/Charmm and Biograf (Molecular Simulations, Inc., Burlington, Mass.).

Several structures of antibody-antigen complexes have been obtained by x-ray crystallography (such as McPC603/phosphorylcholine see (1) Y. Satow, et al, *J. Mol. Biol.*, vol 190, 593–604, (1986) and (2) D. M. Segal, et al, *Proc. Nat. Acad. Sci., USA*, vol. 71, pp. 4298–4302 (1974)). Several such structures are also available in the Protein Data Bank at Brookhaven National Laboratory (F. C. Bernstein, et al, *J. Mol. Biol.* vol. 112, 535–542 (1977)).

Due to the high degree of conserved primary and three-dimensional structure observed in antibody crystal structures (C. Chothia, et al, *Nature*, vol. 342, 877–883 (1989)), reasonable models of the binding site (Fv) domains may also be built using homology modeling techniques when x-ray crystallography data is unavailable (see A. C. R. Martin, J. C. Cheetham, and A. R. Rees, *Proc. Nat. Acad. Sci. USA*, vol. 86, 9268–9272 (1989)). This method requires the primary amino acid sequence of the Fv (antigen binding) domain of the antibody. Information from epitope mapping or site-directed mutagenesis experiments can help determine likely binding interactions with the respective antigen. The techniques necessary for making such determinations are well known to those skilled in the art from the disclosures in references such as Bundle, D. R., *Pure and Appl. Chem.* 61, 1171–1180 (1979). Distances from the antigen to potential amino acid sites for reaction with the modifying group may then be determined.

Suitable clearable linking groups include disulfides and aldehydes. When the preferred thiol modifying group is desired, particularly with the preferred phosphorylcholine binding antibody, an aldehyde cleavable linking group which is subsequently subjected to reduction to yield the thiol modifying group has been found to be the most useful.

When used to modify the phosphorylcholine binding antibody, the aldehyde group reacts with a lysine of the antibody. The lysine is preferably located on the surface of the antibody near the antigen binding site. In one embodiment detailed in the Examples, the aldehyde group reacts with either Lys57H or Lys67H of the heavy chain of McPcC603. In another embodiment detailed in the Examples, preliminary isotopic labeling experiments indicate that the amino acid which is modified on a Streptococcus Group A monoclonal antibody designated St9 is most probably Lys27L of the light chain. Thus, those skilled in the art can identify amino acids which are similarly located in relation to the antigen binding sites on other antibodies by utilizing appropriate computer modeling programs and techniques. Also it is preferable that the modifying group form a covalent bond with the antigen or modified antigen during antigen/antibody binding.

Although any antibody is susceptible to modification as described herein, it has been found that the greatest increase in affinity has been accomplished with the phosphorylcholine binding antibody which can be prepared from a plasmacytoma in tumor bearing BALB/C mice (Goetze and Richards, *Biochemistry* 16, 228 (1977). As explained in greater detail in the examples, the phosphorylcholine binding antibody was modified with a thiol group, and this modified antibody bound the phosphorylcholine antigen with a 400-fold greater affinity than the corresponding unmodified antibody. However, any antibody for which there is a known primary amino acid sequence and a known antigen may be modified by the techniques taught herein. As shown in the Examples, phosphorylcholine binding antibodies, and Group A Streptococcus monoclonal antibodies have been modified by utilizing these techniques. The phospohorylcholine binding antibody reacts with a hapten (the PC antigen), and the Group A Streptococcus antibody reacts with a carbohydrate type antigen.

The strategy and procedure for modifying the Streptococcus Group A antibody (St9) is essentially analogous to that followed for modification of the phosphorylcholine binding antibody (McPC603). Also, similar modified antigen reagents were designed and synthesized.

The differences in modifying St9 as contrasted with McPC603 were: (1) the use of a homology model rather than crystal structure to guide the design of lysine-reactive antigen reagents; (2) the native antigen is a polysaccharide on the outer cell wall of streptococcal Group A bacteria (N-acetylglucosamine (GlCNAc) is the immunodominant carbohydrate of this polysaccharide and the antigenic portion of the synthetic antigens); and (3) the affinity increase of modified St9 antibody over native St9 antibody is approximately 5,000-fold for the maleimide modified antigen reagent (GlcNAc-MAL) and approximately 30,000-fold for the thiopyridyl modified antigen reagent (GlcNAc-TP). The streptococcal Group A antigen is believed to consist of an extracellular polysaccharide with a backbone of L-rhamnose sugar units connected by alternating 1-2 and 1-3 linkages. Every second rhamnose has a branch point with a $\beta$-D-N-acetylglucosamine (GlcNAc) attached thereto (Braun, D. G., *Microbiol. Immunol.* 27, 823 (1983)), as shown below:

Many different methods for determining affinity of antibodies to antigens may be used to determine whether a given chemical modification results in increased affinity. Such methods include solid phase enzyme linked immunoadsorbant assay (ELISA), fluorescence, chemiluminescence, radioimmunoassay (RIA) and other methods known to those skilled in the art. However, a preferred method for determining increased affinity for a modified antibody is to utilize a competition assay in which the ligand (antigen) in solution competes with immobilized bovine serum albumin-phosphorylcholine conjugate for antibody binding. Greater affinity of the ligand for the antibody results in a lower signal seen in the assay. Then, the affinities of the modified antibody and the affinity of the unmodified antibody may be determined and compared.

A minimum requirement of a 10-fold increase in affinity was set as representing a significant increase in the affinity of antibody to antigen. This is an affinity increase which is readily quantifiable and would not be attributable to vagaries of the assay selected for measurement of affinity. It was found that with the preferred phosphorylcholine binding antibody (McPC603) and the preferred thiol modifying group, the thiol modified phosphorylcholine binding antibody exhibited a 400-fold greater affinity for thiopyridyl modified phosphorylcholine antigen than did the unmodified antibody (see FIG. 6). A second antigen, PC-maleimeide exhibited a 1000-fold greater binding affinity for the thiol-modified McPC603 than it did for the unmodified antibody.

The increase in affinity of the thiol modified antibody (both McPC603 and St9) is presumed to be due to the formation of a disulfide bond with the free thiol of the modified antigen. It was also found that incubation of the modified antibody and the thiopyridyl antigen for up to four hours before the competitive assay did not increase the apparent binding between antigen and antibody. This indicates that binding occurs very quickly. The increase in affinity of the modified antibody (McPC603 and St9) for the maleimide modified antigen (PC-MAL and GlcNAc-MAL, respectively, is presumed to be due to the reaction of the antibody's free thiol with a reactive carbon double bond of the maleimide ring to form a thiol ether.

The invention is further described by the following examples which are offered by way of illustration and are not intended to limit the invention in any manner. In these examples all percentages are by weight if for solids and by volume if for liquids, and all temperatures are in degrees Celsius unless otherwise noted.

GENERAL EXPERIMENTAL METHODS

The following general experimental methods were utilized in the Examples set forth below.

NMR spectra were recorded on an IBM/Brucker WP-200SY (200 mHz) (Billerica, Mass.). High resolution fast atom bombardment (FAB) mass spectra (AIG, Inc., Raleigh, N.C.) were obtained with a high performance double focusing AMD 604 instrument with a resolution of 8000 amu. Low-resolution positive ion FAB mass spectra (FAB+) were obtained with a VG Trio-2 quadrupole instrument using either a glycerol or m-nitrobenzyl alcohol sample matrix. Analytical and preparative TLC was performed on glass-backed reverse phase PLKC18F silica gel plates (Whatman). UV/Vis spectra were obtained with a Hewlet Packard HP 8452A Spectrophotometer. A Titertek Multiscan MC instrument was used to obtain absorbance data from microtiter plates.

The PC-BSA conjugate was prepared from BSA and aminophenyl-phosphorylcholine (Sigma) by a slight modification of the diazonium salt coupling method of Cheesebro and Metzger (Biochemistry, vol. 11, 767 (1972)). After adding the diazonium salt to the BSA, the pH of the resulting solution was adjusted to 8.0 and allowed to stand at 4° C. for two days before purification. The McPC603 plasmacytoma was obtained from M. Potter (NCI-NIH, Bethesda, Md. and Hazelhurst Labs, Bethesda, Md.). Crude ascites fluid was collected from BALB/c mice bearing and purified by affinity chromatography using a PC-BSA conjugate.

The St9 antibody was obtained from the American Type Tissue Culture Collection, ATCC No. HB 11260.

EXAMPLE I

Synthesis of Modified Phosphorylcholine Antigens

Figure 3:
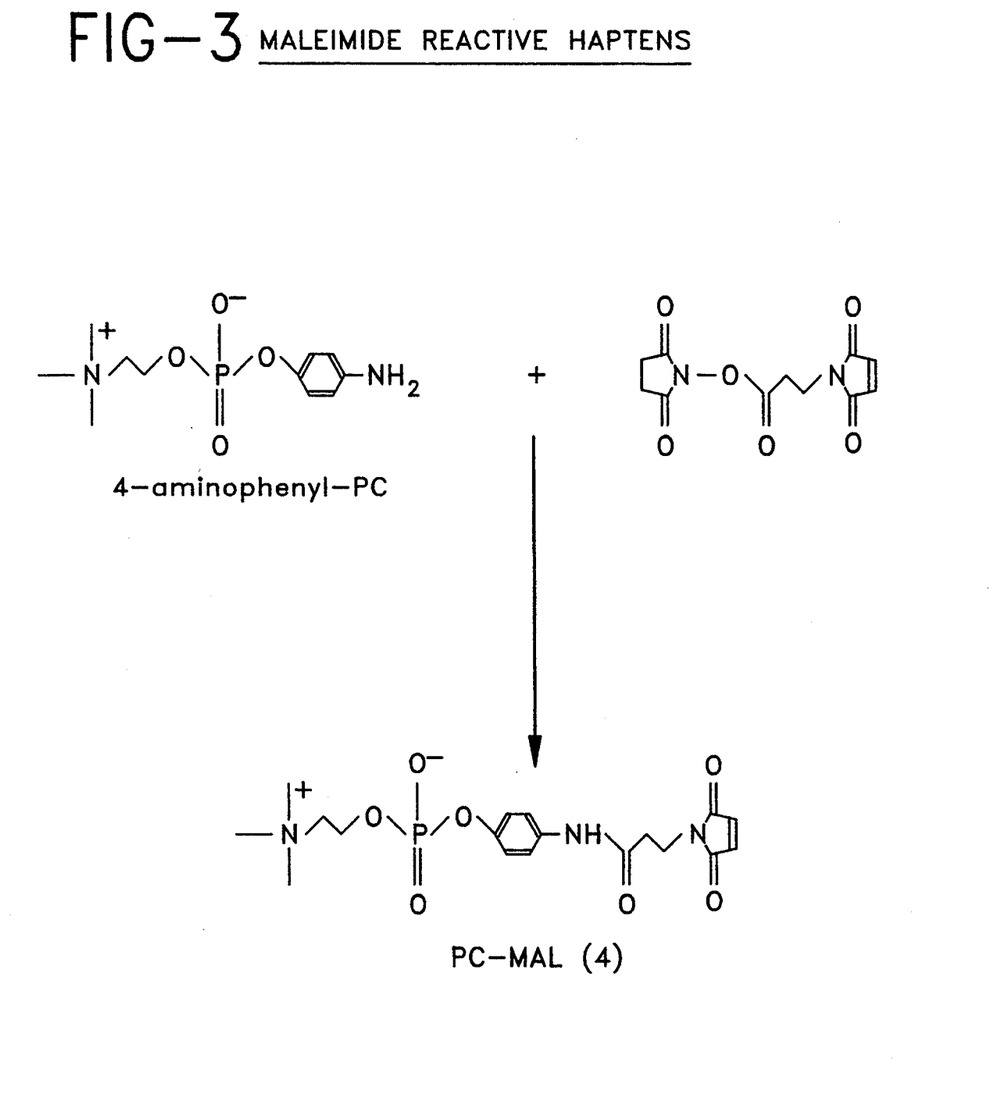
FIG. 3 shows a chemical reaction involved in the preparation of a maleimide modified phosphorylcholine antigen (PC-MAL)

The chemical reactions which take place during the synthesis of the following specified modified phosphorylcholine antigens are shown in FIGS. 2 and 3.

A. Synthesis of 4-[3-(2-pyridyldithio)propionamidyl]-phenyl phosphorylcholine (1)

A 25 mL round bottom flask, fitted with reflux condenser, magnetic stirrer, and heating mantle, was charged with 200 mg (0.730 mmol) of 4-aminophenyl phosphorylcholine, 200 mg (0.642 mmol) of N-succinimidyl 3-(2-pyridyldithio)propionate, and 15 mL of dry methanol. The solution was stirred for 2 hours at ambient temperature, refluxed for 2 hours and then stirred at ambient temperature overnight. The volume of the mixture was reduced to approximately 2 mL and the viscous mixture applied to a thick layer C-18 reverse phase plate. The plate was developed in a 70:30 mixture of methanol:water. After development the plate was air dried, the middle band ($R_f$=0.6) was scraped off and the product eluted from the gel with methanol to yield 137 mg of an oil (40%):

$^1$H NMR (CD$_3$OD) 2.85 (t, 2H), 3.05 (m, 2H), 3.08 (s, 9H), 3.60 (t, 2H), 4.34 (m, 2H), 7.18 (d, 3H), 7.48 (d, 2H), 7.78 (m, 2H), 8.40 (d, 1H); $^{13}$C NMR (CD$_3$OD) 35.4, 36.8, 54.7, 60.8, 67.3, 117.2, 121.4, 121.9, 122.5, 135.4, 139.1, 150.4, 161.2, 171.4; FAB+ MS: Calculated for $C_{19}H_{27}N_3O_5PS_2$: 472.11245, Found: 472.11295 (m-nitro benzyl alcohol).

B. Synthesis of 4-[3-(2-(1,3-dioxolan-2-yl)ethyldithio)-propionamidyl]phenyl phosphorylcholine (2)

A 30 mL round bottom flask, fitted with reflux condenser, magnetic stirrer, and heating mantle, was charged with 110 mg (0.233 mmol) of 4-[3-(2-pyridyldithio)propionamidyl]-phenyl phosphorylcholine, 100 mg (0.746 mmol) of 2-(2-thiolethyl)-1,3-dioxolane, 4 drops of triethylamine, and 15 mL of methanol. This mixture was stirred at ambient temperature for 48 hours and then refluxed for 10 hours. The mixture was then cooled and concentrated under vacuum to an oil. This mixture was applied to a thick layer C-18 reverse phase plate and developed in a 70:30 mixture of methanol:water. After development the plate was air dried, the middle band ($R_f$=0.7) was scraped off and the product was eluted from the gel with methanol. Yield was 38 mg (33%)

$^1$H NMR (CD$_3$OD) 1.85 (m, 2H), 2.59 (m, 4H), 2.84 (q, 2H), 2.97 (s, 9H), 3.41 (m, 3H), 3.69 (m, 4H), 4.13 (bs, 2H), 7.00 (d, 2H), 7.33 (d, 2H); FAB+ MS: Calculated for $C_{19}H_{32}N_2O_7PS_2$: 4495.13766, Found: 495.13886 (m-nitro benzyl aclohol).

C. Synthesis of 4-[3-(3oxo-propyl-dithio)-propionamidyl]phenyl phosphorylcholine (3)

A vial containing 2.6 mg (0.0058 mmol) of 4-[3-(2-(1,3-dioxolan-2-yl)ethyldithio)propionamidyl]phenyl phosphorylcholine (2) and 0.1 mL of a 1:1:4 acetonitrile:water:acetic acid mixture was sealed and heated at 100° C. Conversion of the dioxolane to the aldehyde was monitored by mass spectrometry and was complete after 3 hours. The freshly prepared aldehyde was used immediately in the next step without further purification: FAB+MS: Calculated for $C_{17}H_{28}N_2O_6PS_2$: 451.11199, Found: 451.11799 (m-nitro benzyl alcohol).

D. Synthesis of 4-[3-(1-maleimidyl)-propionamidyl]phenyl phosphorylcholine (4)

To a flask containing 1 mL of 100% ethanol was added 4-aminophenyl phosphorylcholine (11 mg, 0.040 mmol) followed by 3-maleimidyl-propionic acid N-hydroxysuccinimide ester (11 mg, 0.041 mmol). Three drops of water were added to fully dissolve the reactants. After stirring 4 hours, solids had formed and these were removed by filtration through a cotton plug. Evaporation of solvent produced 14 mg (82%) of crude product:

$^1$H NMR (DMSO-d$_6$) 2.55 (m 2H), 3.10 (s, 9H), 3.30–3.80 (m, 4H), 4.12 (m, 2H), 7.01 (s, 2H), 7.05 (d, 2H), 7.40 (d, 2H), 10.12 (br s, 1 H) FAB+MS: Calculated for $C_{18}H_{25}N_3O_7P$: 426.14264, Found: 426.14664 (m-nitro benzyl alcohol).

EXAMPLE 2

Procedure for Modifying McPC603 Antibody with Aldehyde (3)

Figure 4:
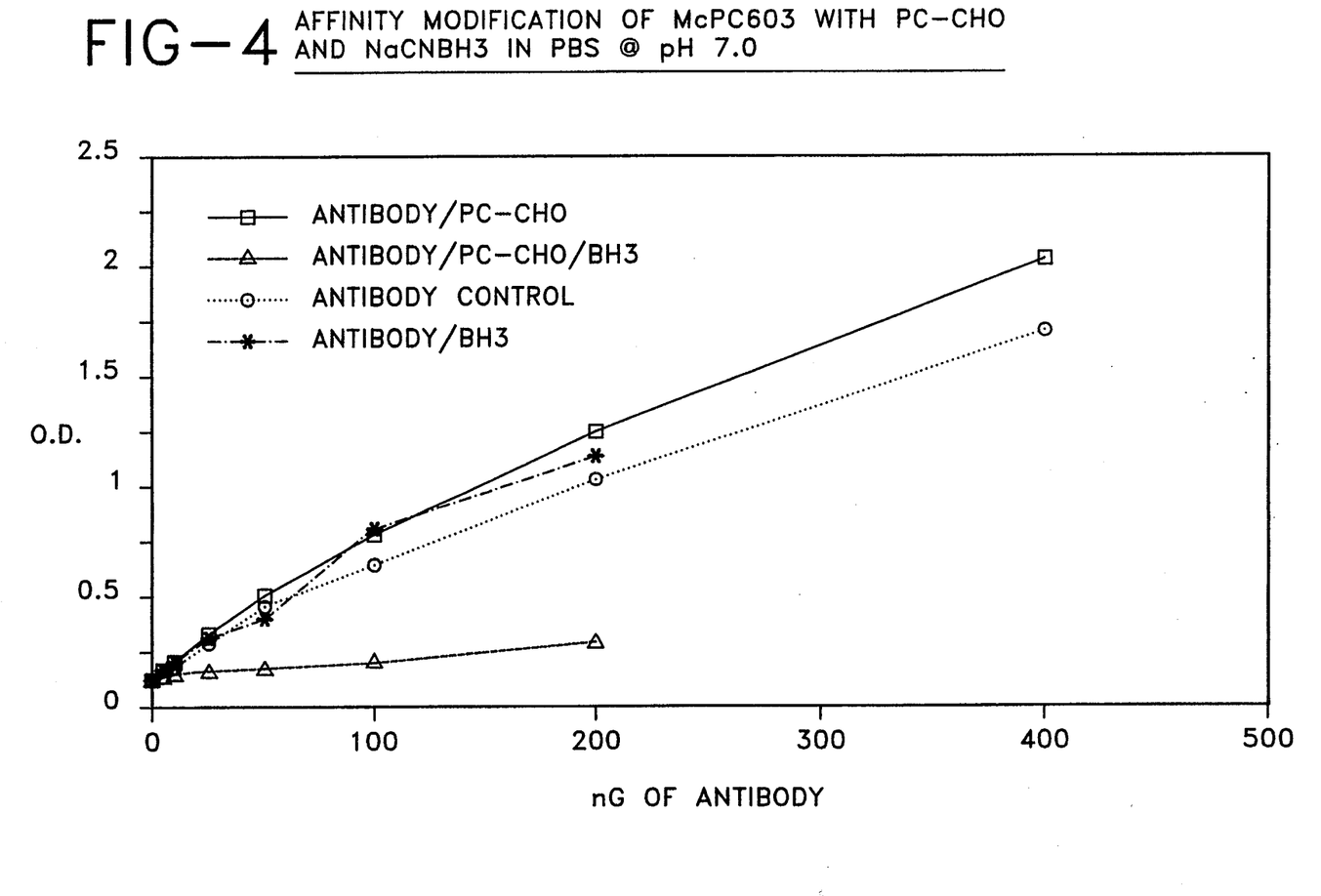
FIG. 4 shows a graphic representation of activity modification of phosphorylcholine binding antibody as compared to controls.

To a 1.0 mg of McPC603 antibody at pH 7.0 in 50 mM PBS buffer at approximately 1.0 mg/mL was added 30 uL of a 46 mM solution of aldehyde (3) in CH$_3$CN:H$_2$O:HOAc 1:1:1. This mixture was incubated at ambient temperature for one hour and then 10 uL of a 192 mM solution of NaCNBH$_3$ in water was added and incubated at 37° C. overnight. This process and the resulting thiol modified phosphorylcholine binding antibody are shown schematically in FIG. 1. Controls were run concurrently with antibody alone incubated at 37° C., antibody incubated with NaCNBH$_3$, and antibody and aldehyde incubated. These solutions were assayed in a standard microtiter tray format, and results are shown in FIG. 4.

Antibody activity was reduced by 90% for the incubation of antibody, aldehyde and NaCNBH$_3$ together, but not the controls. This shows an activity modification of McPC603 which resulted in the antibodies' decreased ability to bind to immobilized PC-BSA. Modified and unmodified antibody were separated using an affinity column of PC attached to sepharose. Antibody was placed on a 2 mL column which had been previously washed and equilibrated with PBS buffer. Ten 1.0 mL fractions were collected and A$_{280}$ were determined. The first 3 fractions, which contained modified antibody were combined and dialyzed against PBS. An activity assay was performed and no activity was noted. Labeling of Modified McPC603 Antibody with Fluorescein The modified McPC603 antibody (3.0 mL of a 1.0 mg/mL solution) was incubated for 1 hour with 3 μL of 1M DTT at room temperature. A 1.4 μL aliquot of 26 mM fluorescein iodoacetamide (Molecular Probes, Eugene, Oreg.) in DMSO was added to the resulting mixture and this was incubated overnight at 4° C. The product was exhaustively dialyzed until background fluorescence was removed. The labeled antibody (50 μL), DTT (4 μL of a 0.5M solution), iodoacetamide (1 μL of a 1M solution), Tris HCl (1 μL of a pH 6.8 1M solution) and 5 μl of a 10% SDS gel solution were heated to 95° C. for 5 minutes. A sample of unlabeled native antibody was treated by an identical procedure. The light and heavy chains of each mixture were separated by 10% SDS PAGE, the gels were divided accordingly, and incorporated label was determined with a fluorescence gel analyzer. All detectable fluorescence resided in the heavy chain of the modified antibody.

EXAMPLE 3

Procedure for Reactivation of Antibody (Formation of McPC603-SH)

Figure 5:
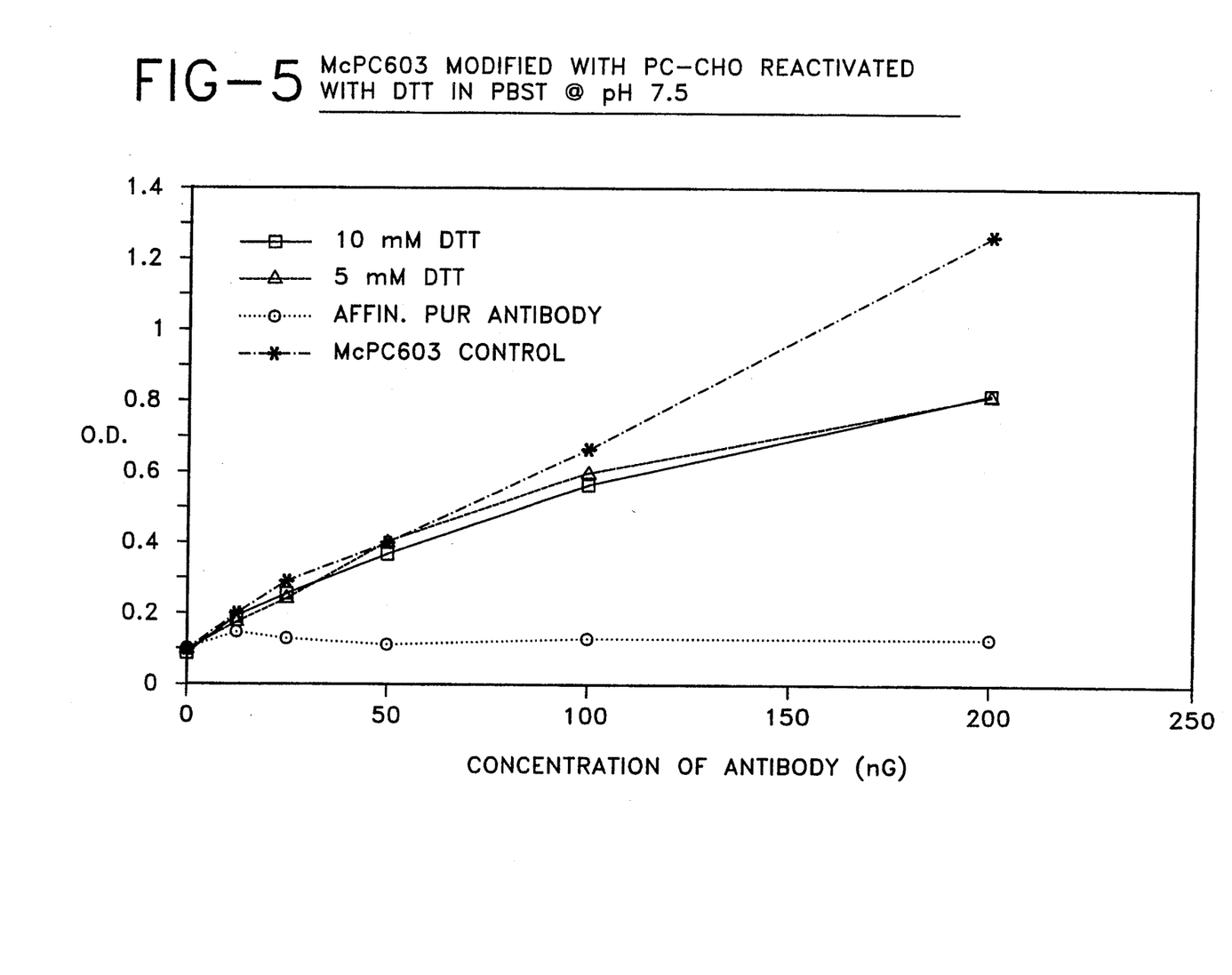
FIG. 5 shows a graphic representation of activity modification of phosphorylcholine binding antibody which has been reactivated with dithiothreitol (DTT) as compared to controls.

Modified antibody from Example 2 was incubated with 10 and 20 mM DTT for 1 hour at ambient temperature. This procedure restored approximately 100% of the antibody activity compared to standards as shown in FIG. 5.

EXAMPLE 4

Competitive Assay of Modified and Unmodified Phosphorylcholine Binding Antibody

A. Preparation of Plates for Activity Assays

Nunc Maxisorb ™ 96 micro well plates were coated with 100 uL/well of PC-BSA at a concentration of 10.0 ug/mL for 2 hours at 37° C. in PBS buffer at pH 7.2. The plates were washed (3×200 uL/well) with PBS buffer, PH 7.2, with 0.05% Tween 20 added (PBST). The plates were then blocked for 2 hours with 200 uL/well 1.0% Fetal Calf Serum (FCS) in PBST. The plates were then washed (3×200 uL/well) and stored desiccated at 4° C. until use.

B. Antibody Activity Assay

Native and modified McPC603 antibody were serially diluted 1:1 with 1.0% FCS in PBST starting at a dilution of 200 ug/mL and ending at a dilution of 12.5 ug/mL. A 100 uL aliquot of each dilution of antibody was added, in duplicate, to microwells coated with PC-BSA. The microwell plates were incubated for 1 hour at 37° C. and then washed (3×200 uL/well) with PBST. A 100 uL sample of a 1:1000 dilution of goat antimouse-horse radish peroxidase conjugate (stock solution 1 mg/mL, Fisher Biotech) was added to the wells, which were then incubated for 1 hour at 37° C. and washed (3×200 uL/well) with PBST. Then, 100 uL of O.P.D. (horse radish peroxidase substrate, SIGMA Chemicals) with 0.083% $H_2O_2$ in citrate/phosphate buffer at pH 5.5 was added to the wells and color development was allowed to proceed for 20 minutes. 50 uL of 4.5N $H_2SO_4$ was then added to stop color development and to stabilize the signal. The optical density (O.D.) of the wells was read at 490 nm and the results are shown in FIGS. 4 and 5.

C. Antibody Competition Assay

Figure 6:
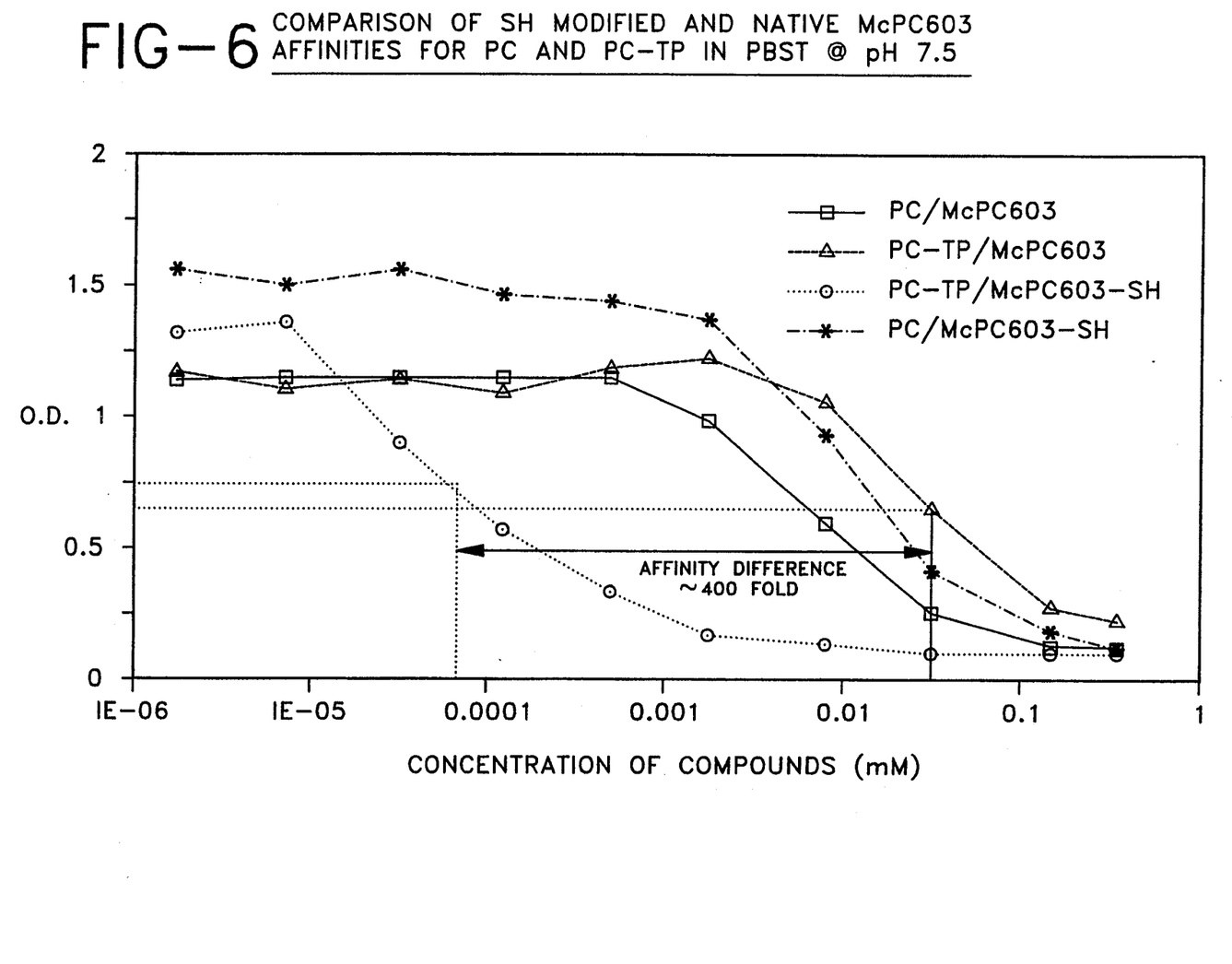
FIG. 6 shows a graphic representation of the increased affinity of a thiol modified phosphorylcholine binding antibody for modified phosphorylcholine antigen as compared to native unmodified antibody.
Figure 7:
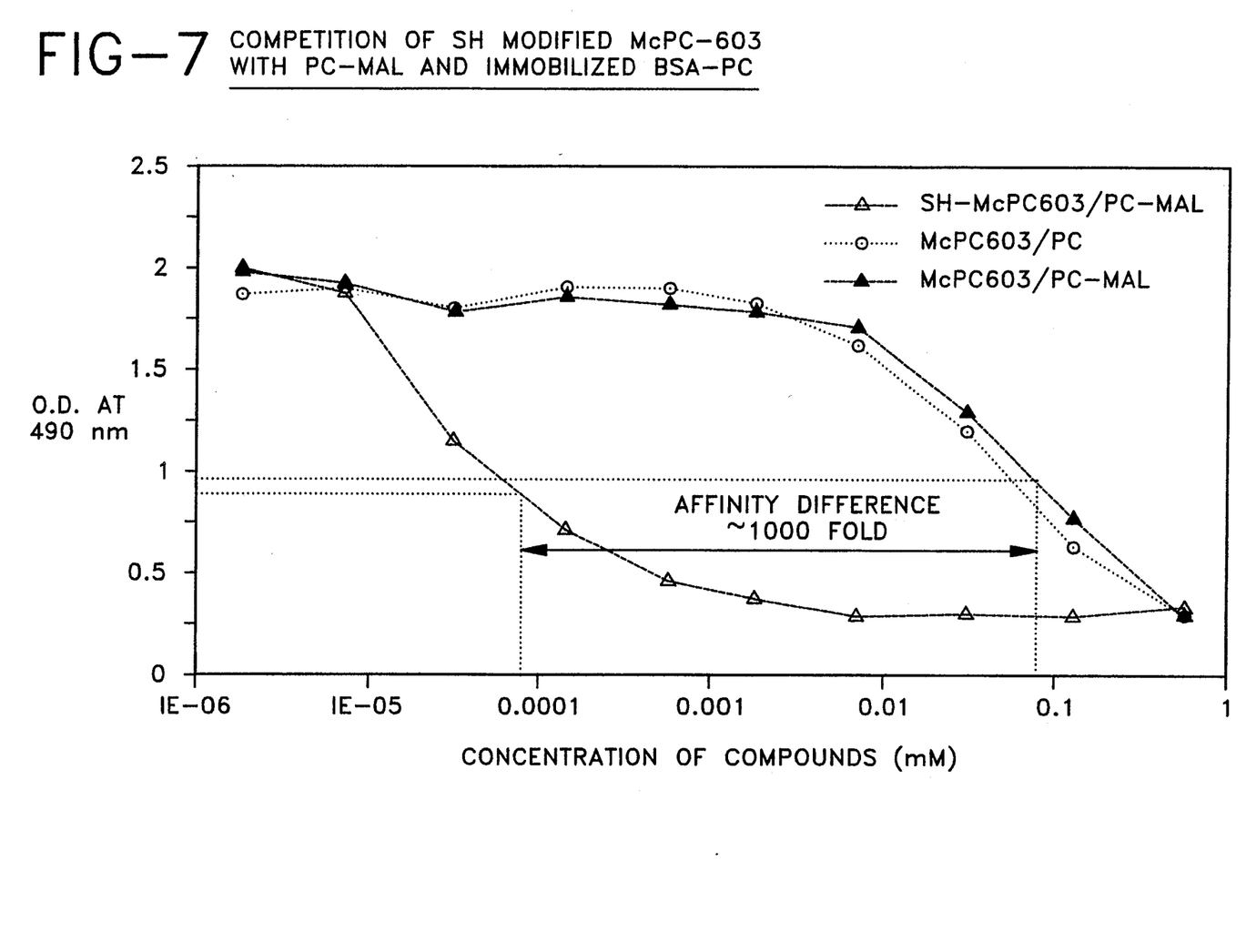
FIG. 7 shows a graphic representation of activity modification of phosphorylcholine binding antibody for PC-MAL antigen as compared to controls.
Figure 8:
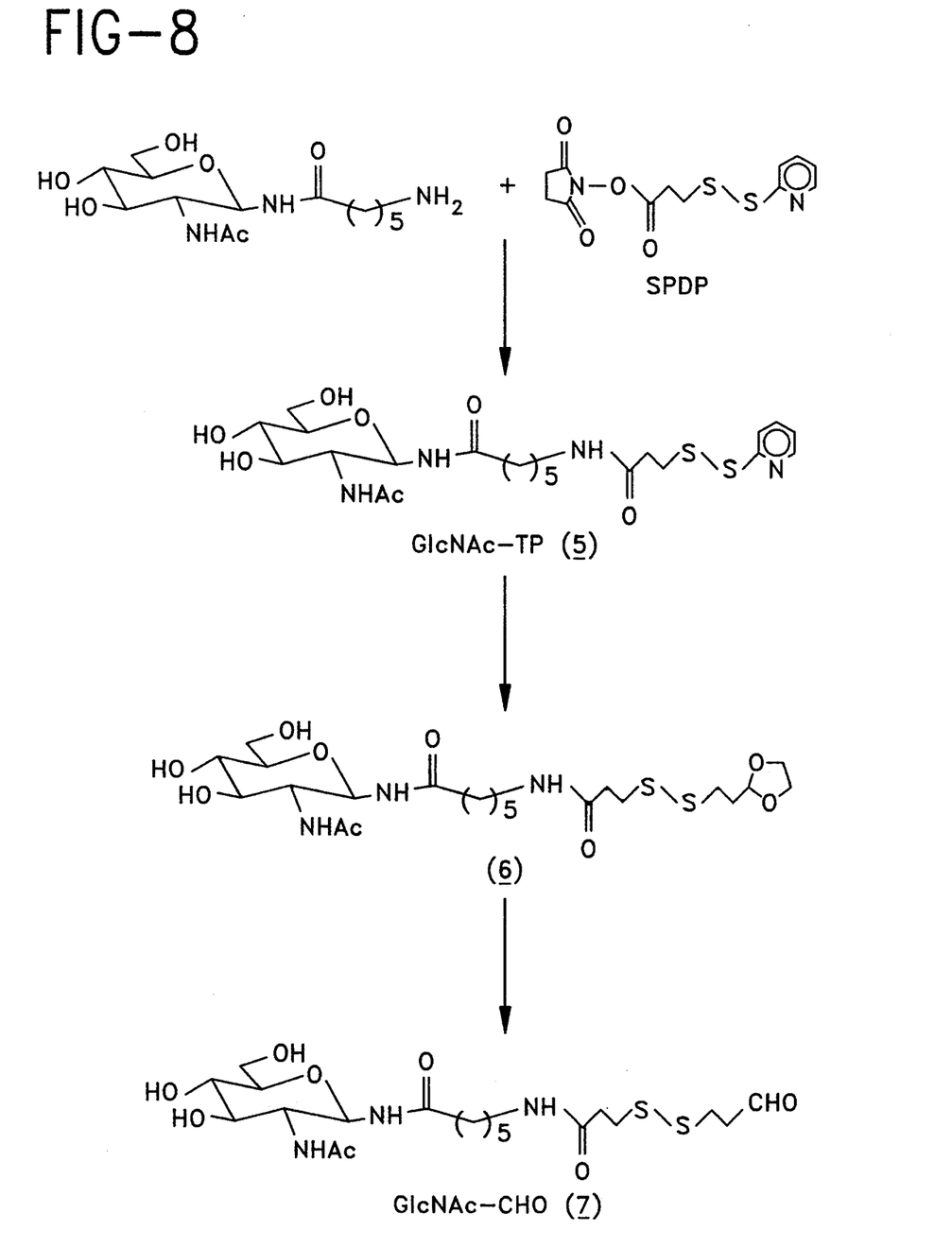
FIG. 8 shows the synthesis of a thiopyridyl modified GlcNAc reagent (GlcNAc-TP) and subsequent preparation of an aldehyde modified antigen reagent (GlcNAc-CHO).
Figure 9:
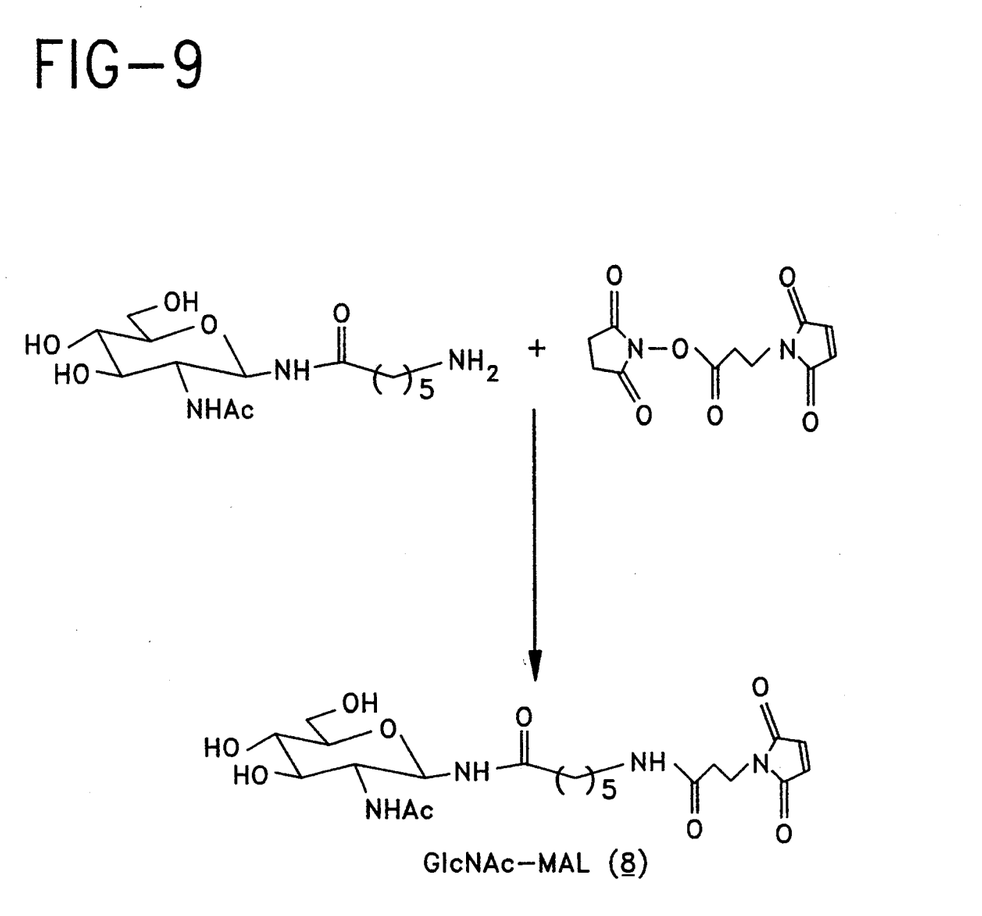
FIG. 9 shows the synthesis of a maleimide modified GlcNAc antigen (GlcNAc-MAL).

The compound to be analyzed by competitive assay was serially diluted 1:3 with 1.0% FCS in PBST staring at a saturating dilution and ending at a non-saturating dilution (usually 6–8 dilutions covering 3–4 logs of concentration. A 50 uL aliquot of 100 uL of each dilution of compound was added, in duplicate, to microwells coated with PC-BSA. A 50 uL sample of a 200 ug/mL solution of native or modified McPC603 antibody was then added to each well that contains compound bringing the volume to 100 uL/well. The plates were incubated for 1 hour at 37° C. and then washed (3×200 uL/well) with PBST. A 100 uL aliquot of a 1:1000 dilution of goat antimouse-horse radish peroxidase conjugate (stock solution 1 mg/mL, Fisher Biotech) was added to the wells which were then incubated for 1 hour at 37° C., and washed (3×200 uL/well) with PBST. 100 uL of O.P.D. with 0.083% $H_2O_2$ in a titrate/phosphate buffer at pH 5.5 was added to the wells and color development was allowed to proceed for 20 minutes. 50 uL of 4.5N $H_2SO_4$ was then added to stop color development and stabilize the signal. The O.D. of the wells was read at 490 nm and the results are shown in FIGS. 6 and 7.

EXAMPLE 5

Preparation and Molecular Modeling of Modified Streptococcus Group A Monoclonal Antibody St9

A molecular model of the St9 antibody Fv region was built based on the experimentally determined sequences of its light and heavy chains, using the Sybyl Composer program (Tripos, Inc., St. Louis, Mo.). First, sequence homologies to respective antibody light or heavy chain domains were determined from a protein database consisting of antibody fragments with known 3D structures. The best ten light chain homologs and the best seven heavy chain homologs were selected and the light and heavy chain domain models were constructed independently. The 3D coordinates of conserved framework regions of the respective homologs were aligned and the correct residues were inserted for the St9 sequence using an RMS fitting procedure to the averaged alpha carbon coordinates. After completion of the framework regions, the hypervariable loop regions (CDRs) were built using coordinates of proteins from the entire Brookhaven database by an alpha-carbon loop searching algorithm similar to that described by Martin, et al (*Proc. Nat. Acad. Sci. USA,* vol. 86, 9268–9272 (1989)). After preliminary energy minization with the backbone atoms constrained in position, the two domains were aligned together by an RMS fit of the conserved backbone regions of the two domains to the corresponding regions in the 4420 fluorescein binding Fab fragment (Brookhaven pdb file 4FAB; this antibody had the highest overall sequence homology to the St9 Fv domain). After manual adjustments of close contacts, the structure was further refined by steepest descent energy minimization with gradual relaxing of side chain and loop residue constraints.

The St9 antibody Fv region model binding site appears to have a distinct "groove" character with a central pocket which can easily accomodate a GlcNAc residue from the Streptococcal Group A polysaccharide antigen. A GlcNAc monosaccharide model was built using coordinates for beta-D-glucose provided with the Sybyl program. This was manually docked in the putative binding pocket and distances from the glycosidic heteroatom (an oxygen in the model, an amide nitrogen in the GlcNAc-CHO and GlcNAc-MAL reagents) to the closest lysine side chain nitrogens were determined ±2 Å: Lys27L (15 Å), Lys67H (19 Å), and Lys54H (18 Å). The distances were used to design the appropriate cleavable linker reagent for modification of the antibody and modified antigens for increased binding to the modified antibody.

EXAMPLE 6

Synthesis of Modified Streptococcus Group A Antigens

The chemical reactions which take place during the synthesis of the following specified modified streptococcus Group A antigens are shown in FIGS. 8 and 9.

A. Synthesis of 2-acetamido-1-[6-(3-(2-pyridyldithio)-3-propionamidyl)-1-oxo-hexyl]-amino-1,2-dideoxy- -D-glucose (5)

A 50 mL round bottom flask equipped with a magnetic stirrer was charged with 336 mg (1.00 mmol) of 2-acetamido-1-(6-amino-1-oxo-hexyl)-1,2-dideoxy- -D-glucose (Sigma Chemical Co., St. Louis, Mo.), 314 mg (1.00 mmol) of N-Succinimidyl 3-(2-pyridyldithio)-propionate (SPDP, Sigma), and 15 mL of dry N,N-dimethylformamide. The reactants slowly dissolved to form a yellow solution. This solution was stirred for 15 hours at ambient temperature under an argon atmosphere. The solvent was evaporated under reduced pressure (1 mm, 40° C.) and the resulting solid was recrystallized from methanol and ether to give 500 mg (94%) of product: TLC (C-18 reverse phase 1:1 methanol/water, UV detection) $R_f=0.3$;

$^1$H NMR (CD$_3$OD) 1.20–1.65 (m, 6H), 1.97 (s, 3H), 2.20 (t, 2H), 2.61 (t, 2H), 3.02–3.82 (m, 10H), 4.95 (d, 1H), 7.23 (m, 1H), 7.83 (m, 2H), 8.40 (m, 1H); $^{13}$C NMR (CD$_3$OD) 22.5, 26.0, 27.1, 29.7, 35.7, 35.8, 36.8, 40.0, 55.9, 62.4, 71.6, 76.0, 79.4, 80.1, 120.9, 138.8, 150.1, 161.0, 172.8, 174.0, 176.2; FAB+ MS (glycerol): Calculated for [MH]+ C$_{22}$H$_{35}$N$_4$O$_7$S$_2$: 531.19525 amu, Found: 531.19025.

B. Synthesis of 2-acetamido-1-[6-(3-2-(1,3-dioxolan-2-yl)-ethyldithio)-3-propionamidyl)-1-oxo-hexyl]-amino-1,2-dideoxy- -D-glucose (6)

A 50 mL round bottom flask was charged with 45 mg (80 μmol) of compound 5, 40 mg (300 μmol) of 2-(2-thiolethyl)-1,3-dioxolane, 4 drops of triethylamine, and 3 mL of dry N,N-dimethylformamide. This mixture was stirred at ambient temperature for 48 hours under argon and concentrated to an oil under reduced pressure. Trituration from a 1:1 ether/methanol solution yielded 40 mg of a solid (85%). This material was homogeneous by TLC (C-18 reverse phase 1:1 methanol/water, $R_f=0.3$) and gave a dark stain after development of the TLC plate with a 50:1:1 acetic acid/sulfuric acid/anisaldehyde mixture and heating. Unlike compound 5, this product showed no UV activity on the TLC plate prior to this treatment.

$^1$H NMR (CD$_3$OD) 1.3–1.6 (m), 1.95 (s, NAc CH$_3$), 2.0 (t), 2.2 (t), 2.55 (t), 2.75 (t), 2.9 (t), 3.1 (t), 3.3–4.0 (m); $^{13}$C NMR (CD$_3$OD) 22.6, 26.0, 27.1, 29.7, 33.4, 34.4, 34.8, 36.8, 40.0, 44.9, 55.9, 62.4, 65.7, 71.6, 76.0, 79.4, 80.1, 103.8, 173.3, 174.1, 176.4; FAB+ MS (glycerol): Calculated for [MH]+ C$_{22}$H$_{40}$N$_3$O$_9$S$_2$: 554.22003. Found: 554.22503.

C. Synthesis of 2-acetamido-1-[6-(3-(3-oxopropyldithio)-propionamidyl)-1-oxo-hexyl]-amino-1,2-dideoxy- -D-glucose (7)

A vial containing 2.5 mg (0.0058 mmol) of compound 6 and 0.3 mL of a 2:2:1 acetonitrile:water:acetic acid mixture was sealed and heated at 100° C. for 3 hours. Conversion of the dioxolane to the aldehyde was monitored by mass spectrometry and TLC (C-18 reverse phase 1:1 methanol/water). The product aldehyde had an $R_f=0.5$ and gave a dark stain after development of the TLC plate with a 50:1:1 acetic acid/sulfuric acid/anisaldehyde mixture and heating. For best results, the freshly prepared aldehyde was used immediately in the next step (modification of the St9 antibody) without further purification: Low resolution FAB+ MS (glycerol): Calculated for [MH]+ C$_{20}$H$_{36}$N$_3$O$_8$S$_2$: 510.19441. Found: 510.

D. Synthesis of 2-acetamido-1-[6-(3-(1-maleimidyl)-propionamidyl)-1-oxo-hexyl]-amino-1,2-dideoxy- -D-glucose (8)

A 50 mL round bottom flask equipped with a magnetic stirrer was charged with 100 mg (0.300 mmol) of 2-acetamido-1-(6-amino-1-oxo-hexyl)-1,2-dideoxy- -D-glucose, 85 mg (0.32 mmol) of beta-maleimidopropionic add N-hydroxy-succinimide ester and 10 mL of dry N,N-dimethylformamide. This mixture was stirred for 48 hours at ambient temperature under argon. The solvent was evaporated under reduced pressure (1 mm, 40° C.). The resulting solid was rinsed with acetonitrile and filtered to yield 132 mg (82%) of white solid: TLC (C-18 reverse phase 1:1 methanol/water, acetic acid/sulfuric acid/anisaldehyde detection) $R_f=0.7$;

$^1$H NMR (DMSO- d$_6$) 1.85 (s, N-Ac CH$_3$), 7.00 (s, maleimide CH), 7.80–8.00 (m, amide NH); $^{13}$C NMR (CD$_3$OD) 22.5, 26.0, 27.1, 29.6, 35.2, 35.4, 36.8, 39.9, 55.9, 62.4, 71.6, 76.0, 79.4, 80.1, 135.2, 171.8, 172.5, 174.0, 176.2; Low resolution FAB+ MS (m-nitrobenzyl alcohol): Calculated for [MH]+ C$_{21}$H$_{32}$N$_4$O$_9$: 485.22475. Found: 485.

EXAMPLE 7

Procedure for Modifying St9 Antibody With Aldehyde (7)

To a 350 uL solution of St9 (2 mg/mL) in 50 mM PBS buffer at pH 7.2 was added 40 uL of a 17 mM solution of freshly prepared aldehyde (7) in CH$_3$CN:H$_2$O:HOAc 2:2:1. The pH was adjusted back to 7.2 and was incubated at ambient temperature for one hour. A 10 μL aliquot of a 128 mM solution of NaCNBH$_3$ was added and the mixture was allowed to stand for 20 hours at ambient temperature. Controls run concurrently were antibody alone, antibody with NaCNBH$_3$, and antibody plus aldehyde (7). The first solution, antibody modified with aldehyde and NaCNBH$_3$ was dialyzed against PBS (50 mM, pH 7.2) overnight. The dialysis product was purified by elution with PBS buffer through an affinity column prepared from 4 mL N-acetylglucosamine 6% on beaded agarose (Sigma). Ten fractions were collected. The first three fractions contained modified antibody which did not bind to the affinity column (total volume 5 mL). The A$_{280}$ of these fractions was determined and evaluation with a micro-BCA assay (Pierce) gave a concentration of 90 μg/mL (65% yield).

Activities of the affinity-purified modified St9 antibody, the original St9 antibody, and affinity-purified St9 antibody after incubation for one hour with 20 mM DTT were compared (see FIG. 10) in a standard microtiter tray format. There was no detectable binding of the modified antibody without DTT, but the modified antibody after incubation with DTT demonstrated over 90% of the binding affinity was restored in comparison to the native St9 antibody.

Labeling St9 Antibody with Tritium

A solution of 2.0 mg of St9 antibody (250 gL of a 7.99 mg/mL solution) and 10 μL of a 5.4 mg/mL solution of GlcNAc-CHO (compound 7) were vortexed and incubated at room temperature for 15 minutes. An ampule (1.53 mmol, 6.3 ci/mmol) of NaCNB$^3$H$_3$ (Amersham Corp., Arlington Heights, Ill.) was opened in a fume hood and dissolved in 100 82 L of pH 7.5 PBS. A 50 μL aliquot of this solution was added to the antibody and aldehyde solution and incubated at room temperature overnight. The modified antibody was purified by affinity chromatography as described for the non-labeled antibody, followed by exhaustive dialysis until all tritium was removed from the dialysis buffer. The labeled antibody (50 μL), DTT (4 μL of a 0.5M solution), iodoacetamide (1 μL of a 1M solution), Tris HCl (1 μL of a pH 6.8 1M solution) and 5 μL of a 10% SDS gel solution were heated to 95° C. for 5 minutes. A sample of unlabeled native antibody was treated by an identical procedure. The light and heavy chains of each mixture were separated by 10% SDS PAGE, the gels were divided accordingly, and incorporated label was determined with a scintillation counter. All detectable signal was found in the labeled antibody's light chain gel fraction.

EXAMPLE 8

Procedure for Reactivation of Modified St9 Antibody

Figure 10:
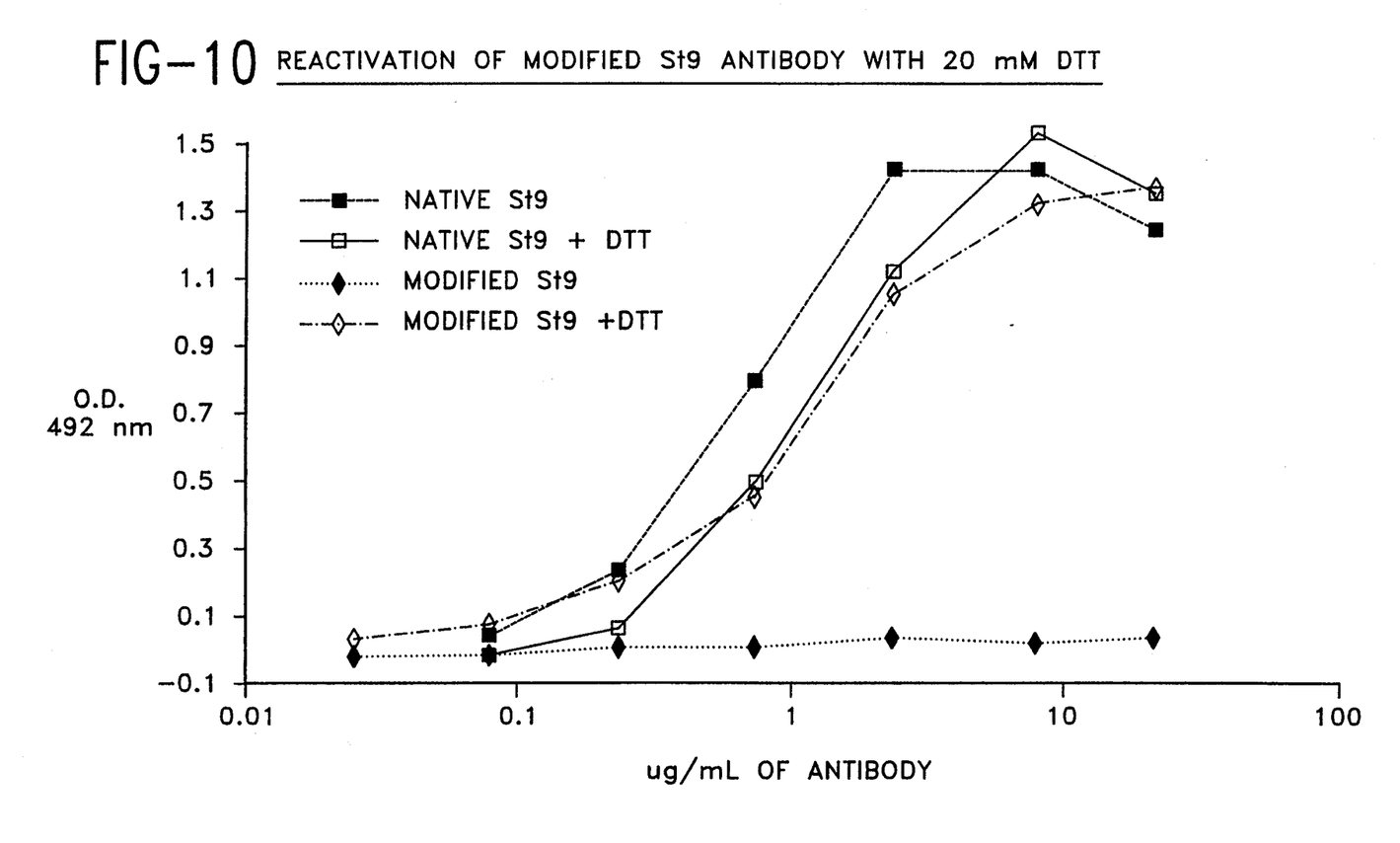
FIG. 10 shows a graphic comparison of affinity purified modified streptococcus Group A binding antibody before and after treatment with DTT to regenerate binding affinity, as compared to controls.

The affinity-purified St9 antibody was incubated for one hour at ambient temperature with 20 mM DTT. The DTT was subsequently removed by several cycles of centrifugal concentration using Centricon-30 devices (Areicon, Beverly, Mass.) spun at 4000 rpm and 4° C. A control of native St9 antibody was treated in a similar fashion. Both samples were diluted as described below and used directly in competition assays. The results of the reactivation are shown in FIG. 10.

EXAMPLE 9

Competitive Assay of Modified and Unmodified Streptococcus Group A Monoclonal Antibody A. Preparation of Plates for Activity Assays Nunc Maxisorb TM 96 micro well plates were coated with 50 uL/well of heat-killed Streptococcus Group A organisms diluted in a carbonate buffer at pH 9.6 to $1 \times 10^7$ organisms/mL. These were allowed to air dry in a hood for 18 hours, then blocked with 200 uL/well with 1.0% Fetal Calf Serum (FCS) in PBS for one hour at 37° C. The plates were washed (3×200 uL/well) with PBS buffer, pH 7.2, with 0.05% Tween 20 added (PBST) and stored at 4° C. until used.

B. Antibody Activity Assay

Native St9 antibody and modified St9 antibody were diluted with 1% FCS in PBST to give a top concentration of 20 μg/mL and serially diluted 1:2 in the same buffer to give lower concentrations. To a microtiter tray, prepared as described above, 100 μL of each dilution of antibody was added in duplicate. The plates were incubated for 1 hour at 37° C. and then washed (3×200 μL/well) with PBST. Next, 100 μL of a 1:1000 dilution of goat antimouse IgG/horse radish peroxidase conjugate (stock solution 1 mg/mL, Fisher Biotech) was added to each well, the plate was incubated for 1 hour at 37° C., then was washed (3×200 μL/well) with PBST. To each well 100 μL of o-phenylenediamine (HRP substrate, SIGMA Chemicals) with 0.083% $H_2O_2$ in citrate/phosphate buffer at pH 5.5 was added and the color development was allowed to proceed for 20 minutes. At this time 50 μL of 4.5N $H_2SO_4$ was added to stop color development and to stabilize the signal. The O.D. of each well was determined at 490 nm with a Titertek plate reader.

C. Antibody Competition Assay

Figure 11:
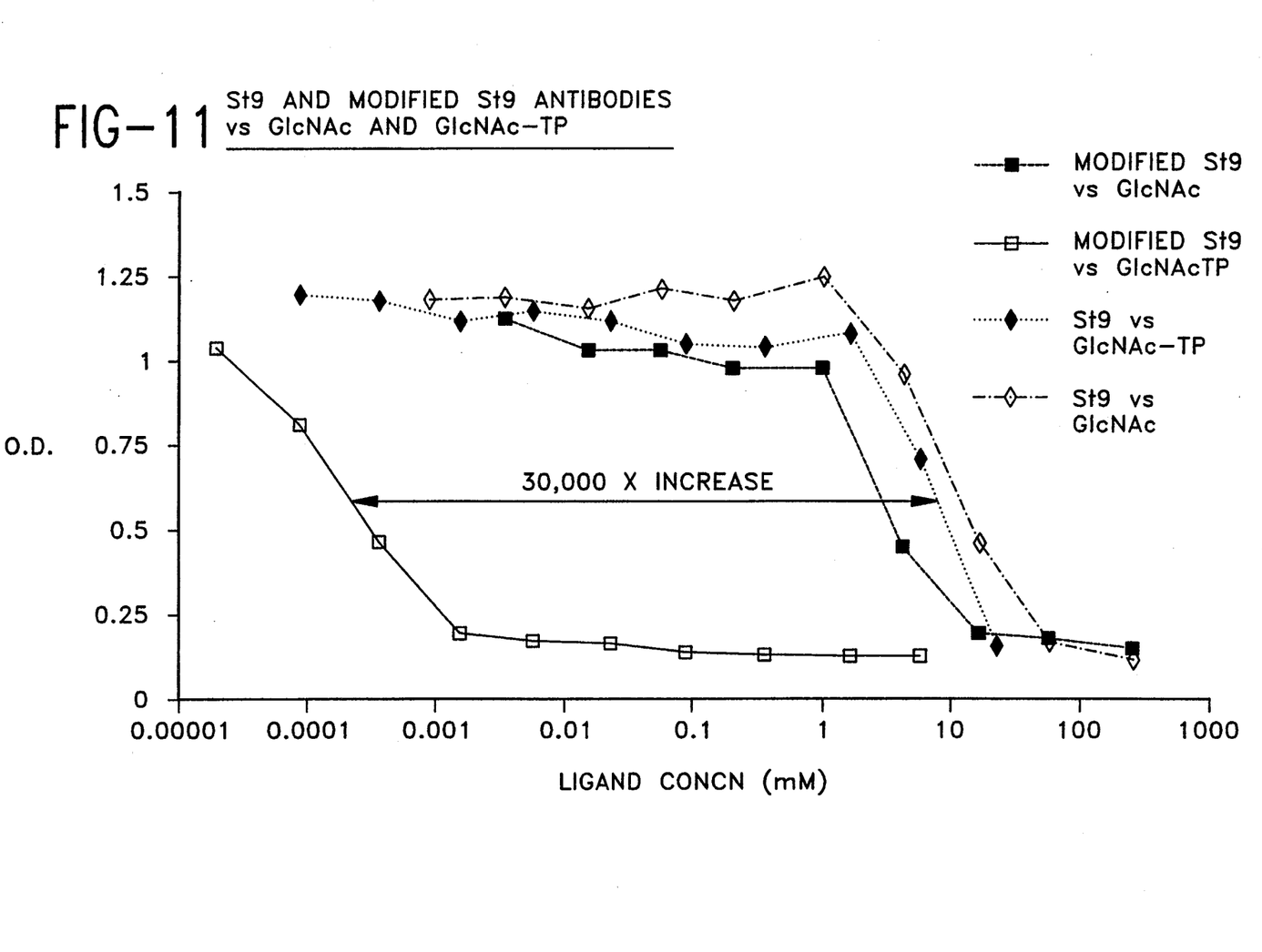
FIG. 11 shows a graphic representation of the increased affinity of a thiol modified streptococcus Group A binding antibody for modified antigen GlcNAc-TP as compared to the native antibody.
Figure 12:
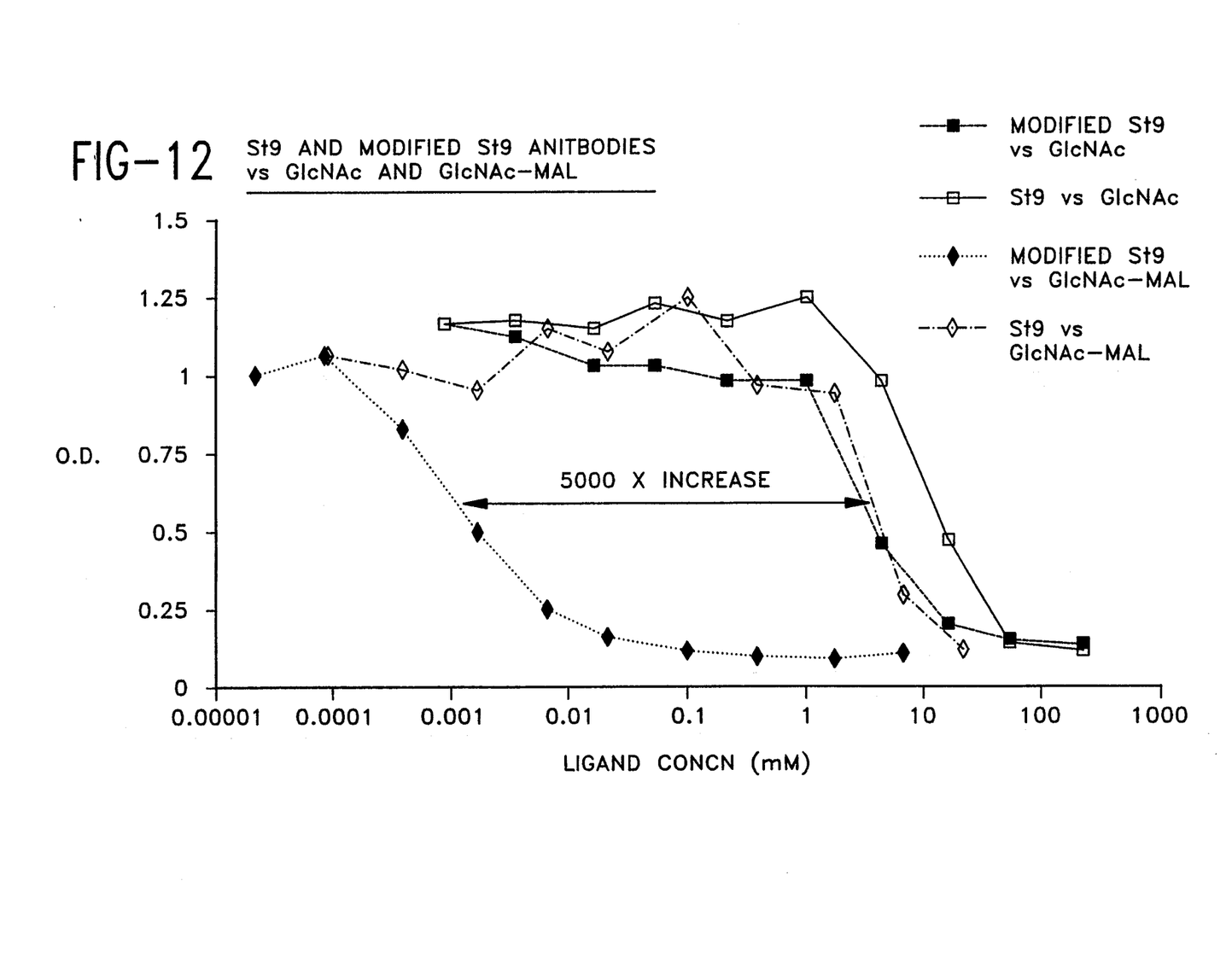
FIG. 12 shows a graphic representation of the increased affinity of a thiol modified streptococcus Group A binding antibody for modified antigen GlcNAc-MAL as compared to the native antibody.

This assay compared native St9 antibody with affinity-purified St9 after treatment with DTT as described above. The compounds analyzed by competitive assay were the thiopyridyl derivative (GlcNAc-TP, 7), maleimide (GlcNAc-MAL, 8), and N-acetyl-glucosamine (GlcNAc, Sigma). Stock solutions of these compounds were prepared and serially diluted 1:3 with 1.0% FCS in PBST starting at a saturating dilution and ending at a non-saturating dilution, typically coveting approx. 4–5 logs in concentration. To the previously prepared micro-titer plates 50 μL of each dilution of compound was added in duplicate. These were allowed to stand for 1 hour at ambient temperature. At this time 50 μL of a 10 mg/mL solution of native St9 antibody or 7 mg/mL solution of reactivated modified St9 antibody were added to each well that contains compound bringing the volume to 100 μL/well. Plates were incubated for 1 hour at 37° C. and developed in a manner identical to the activity assay described above. The results are presented in FIGS. 11 and 12.

Other modifications of the above described embodiments of the invention which are obvious to those of skill in the art of molecular biology and related disciplines are intended to be within the scope of the following claims.

What is claimed is:

1. A thiopropyl modified antibody wherein a thiopropyl moiety is located on the antibody such that a covalent bond is formed between the thiopropyl moiety, which has been reactivated with a thiol-containing group, and an antigen, which has been modified by a maleimide or a thiol-containing group to increase the antigen-antibody binding affinity.

2. The modified antibody of claim 1 wherein the affinity of the modified antibody for the antigen is at least 10-fold greater than the affinity of an unmodified antibody for the antigen.

3. The modified antibody of claim 1 wherein the covalent bond is a reversible covalent bond.

4. The modified antibody of claim 1 wherein the antibody is selected from the group consisting of a phosphorylcholine binding antibody and a Streptococcus Group A antibody.

5. The modified antibody of claim 4 wherein the antibody is a phosphorylcholine binding antibody.

6. The modified antibody of claim 4 wherein the antibody is a Streptococcus Group A antibody.

* * * * *